(12) United States Patent
Lee et al.

(10) Patent No.: US 11,795,199 B2
(45) Date of Patent: Oct. 24, 2023

(54) **PEPTIDE TARGETING *MYCOBACTERIUM TUBERCULOSIS* TOXIN-ANTITOXIN SYSTEM AND USE THEREOF**

(71) Applicant: Seoul National University R&DB Foundation, Seoul (KR)

(72) Inventors: Bong-Jin Lee, Seoul (KR); Sung-Min Kang, Seoul (KR); Do-Hee Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 17/811,848

(22) Filed: Jul. 11, 2022

(65) Prior Publication Data

US 2022/0348612 A1 Nov. 3, 2022

Related U.S. Application Data

(62) Division of application No. 16/632,867, filed as application No. PCT/KR2018/008680 on Jul. 31, 2018, now abandoned.

(30) Foreign Application Priority Data

Jul. 31, 2017 (KR) ........................ 10-2017-0096784

(51) Int. Cl.
*C07K 7/08* (2006.01)
*A61K 38/00* (2006.01)

(52) U.S. Cl.
CPC ................ *C07K 7/08* (2013.01); *A61K 38/00* (2013.01)

(58) Field of Classification Search
CPC .................................. C07K 7/08; A61K 38/00
See application file for complete search history.

(56) References Cited

U.S. PATENT DOCUMENTS

| 2007/0298043 | A1 | 12/2007 | Gazit et al. |
| 2010/0234287 | A1 | 9/2010 | Inouye et al. |
| 2011/0028697 | A1 | 2/2011 | Sano et al. |
| 2013/0295017 | A1 | 11/2013 | Cheung et al. |
| 2013/0330335 | A1 | 12/2013 | Bremel et al. |

FOREIGN PATENT DOCUMENTS

| CN | 104211787 A | 12/2014 |
| JP | 2007-039398 A | 2/2007 |
| KR | 10-2009-0013762 A | 2/2009 |
| KR | 10-2016-0140137 A | 12/2016 |

OTHER PUBLICATIONS

International Search Report from parent PCT Application No. PCT/KR2018/008680, 7 pages (dated Jan. 31, 2019).
Cole et al., "Deciphering the biology of *Mycobacterium tuberculosis* from the complete genome sequence," *Nature* 393: 537-544 (1998).

*Primary Examiner* — Amber D Steele
(74) *Attorney, Agent, or Firm* — KLARQUIST SPARKMAN, LLP

(57) ABSTRACT

The present invention relates to a peptide targeting a toxin-antitoxin system of *Mycobacterium tuberculosis* and a use thereof. Specifically, the antibiotic peptide of the present invention inhibits the formation of a toxin-antitoxin complex of *Mycobacterium tuberculosis* without affecting an active site of the toxin, thereby inducing the death of *Mycobacterium tuberculosis* by means of a separated toxin. Therefore, the antibiotic peptide can be usefully used as an antibiotic composition against *Mycobacterium tuberculosis*.

7 Claims, 11 Drawing Sheets

Specification includes a Sequence Listing.

PEPTIDE TARGETING *MYCOBACTERIUM TUBERCULOSIS* TOXIN-ANTITOXIN SYSTEM AND USE THEREOF

CROSS REFERENCE TO RELATED APPLICATIONS

This is a divisional of U.S. patent application Ser. No. 16/632,867, filed Jan. 21, 2020, which is the § 371 U.S. National Stage of International Application No. PCT/KR2018/008680, filed Jul. 31, 2018, which claims the benefit of Korean Application No. 10-2017-0096784, filed Jul. 31, 2017. The prior applications are incorporated herein by reference in their entirety.

BACKGROUND OF THE INVENTION

1. Field of the Invention

The present invention relates to a peptide targeting a toxin-antitoxin system of *Mycobacterium tuberculosis* and a use thereof.

2. Description of the Related Art

Tuberculosis is an acute and chronic disease which is infectious and contagious that can occur anywhere in the body. It is a terrible disease that can even lead to death. Approximately 85% of tuberculosis is developed in the lung and can be spread to any organ in the body through blood stream or lymph nodes. Tuberculosis is transmitted through the air from cough, runny nose and sputum of a patient. Approximately 9 million people were infected with tuberculosis in 2013, among which about 1.5 million people were dead. In addition, because of the emergence of multidrug-resistant tuberculosis and even fully resistant tuberculosis, it is requested to develop a novel antimicrobial agent to treat *Mycobacterium tuberculosis*.

A toxin-antitoxin gene was first known to play a certain role in maintaining *E. coli* plasmid. When the plasmid containing the toxin-antitoxin gene is lost, the toxin with a stable structure is retained, but the antitoxin protein with an unstable structure is degraded, leading to the destruction of *E. coli* eventually. Since the toxin-antitoxin gene was first identified, it has been found that the toxin-antitoxin gene is present not only in the plasmid but also in the chromosome of *E. coli*. It is known that the gene above is involved in multidrug resistance, biofilm formation and growth inhibition under stress situations.

Toxin-antitoxin systems can be largely divided into three types (Type I, II and III). In type I system, an antitoxin in the form of RNA binds to a toxin in the form of RNA to eliminate the toxicity. In type II system, an antitoxin in the form of protein binds to a toxin in the form of protein to eliminate the toxicity. In type III systems, an antitoxin in the form of RNA binds to a toxin in the form of protein to eliminate the toxicity.

Among these three types, type II system has been most studied. In type II system, toxin and antitoxin genes are coded through operon. Under the difficult external conditions for bacteria, such as elevated temperature or depletion of nutrients, unstable antitoxins are decomposed by stress-inducing proteolytic enzymes and accordingly cannot neutralize the toxin's toxicity, resulting in cell death. The largest part of type II system is VapBC family, and the toxin portion (VapC) of the VapBC family is known to inhibit cell growth based on the RNase activity thereof.

If the formation of the toxin-antitoxin complex can be artificially inhibited, the toxic toxin would not be neutralized and therefore cell would be eventually dead. Thus, the toxin-antitoxin system is an attractive target for the development of novel antibiotics.

In *Mycobacterium tuberculosis*, more than half of the toxin-antitoxin systems are found to belong to VapBC family. Such VapBC family is involved in the extreme incubation period and drug resistance of *Mycobacterium tuberculosis*.

Thus, the present inventors tried to develop a therapeutic agent for tuberculosis targeting the toxin-antitoxin protein complex. In the course of our study, the inventors identified the structure of the VapBC26 complex of *Mycobacterium tuberculosis*, based on which the inventors designed a peptide that can obstruct the formation of a toxin-antitoxin protein complex and confirmed that the peptide was able to inhibit the formation of the toxin-antitoxin protein complex in vitro successfully, leading to the completion of the present invention.

SUMMARY OF THE INVENTION

It is an object of the present invention to provide a peptide targeting a toxin-antitoxin system of *Mycobacterium tuberculosis* and a composition comprising the same as an active ingredient.

To achieve the above object, the present invention provides an antibiotic peptide that inhibits the binding of an antitoxin protein to any one or more residues selected from the group consisting of α3 and α4 of a *Mycobacterium tuberculosis* toxin protein.

The present invention also provides an antibiotic composition against *Mycobacterium tuberculosis* comprising the antibiotic peptide as an active ingredient.

The present invention also provides an antibiotic quasi-drug against *Mycobacterium tuberculosis* comprising the antibiotic peptide as an active ingredient.

The present invention also provides an antibiotic external preparation against *Mycobacterium tuberculosis* comprising the antibiotic peptide as an active ingredient.

The present invention also provides a method for preventing, ameliorating or treating *Mycobacterium tuberculosis* comprising a step of administering the antibiotic peptide to a subject.

In addition, the present invention provides a use of the antibiotic peptide for the preparation of antibiotics against *Mycobacterium tuberculosis*.

Advantageous Effect

The antibiotic peptide of the present invention inhibits the formation of a toxin-antitoxin complex of *Mycobacterium tuberculosis* without affecting an active site of the toxin, thereby inducing the death of *Mycobacterium tuberculosis* by means of a separated toxin. Therefore, the antibiotic peptide can be usefully used as an antibiotic composition against *Mycobacterium tuberculosis*.

SEQUENCE LISTING

Figure 1A:
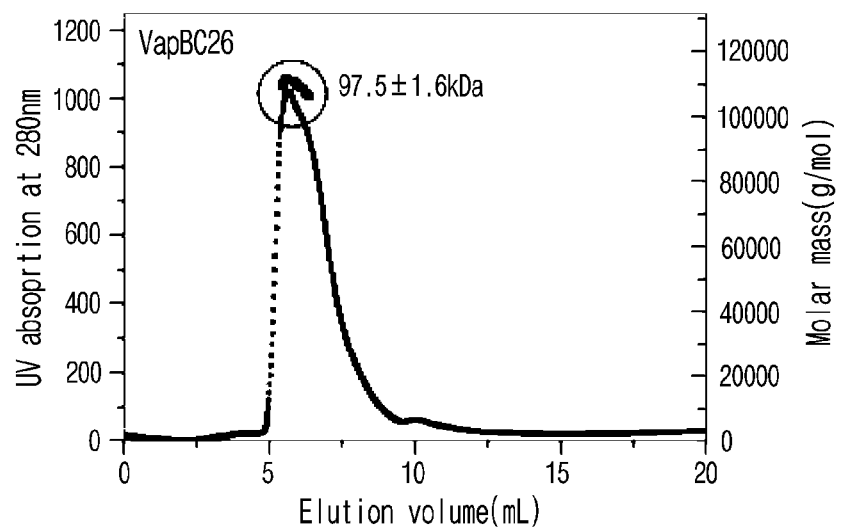
FIGS. 1a and 1b are diagrams showing the results of multi-angle light scattering (MALS) combined with size exclusion chromatography performed to determine the structures of VapB26 and VapBC26.

The Sequence Listing is submitted in ST.26 format in the form of the file named 7037-100905-02_Sequence_Listing.txt, which was created on Jul. 11, 2022, and is 27.5 KB, and is incorporated by reference herein.

DESCRIPTION OF THE PREFERRED EMBODIMENTS

Hereinafter, the present invention is described in detail.

The present invention provides an antibiotic peptide that inhibits the binding of an antitoxin protein to any one or more residues selected from the group consisting of a3 and a4 of a *Mycobacterium tuberculosis* toxin protein.

The said peptide can be synthesized by the conventional chemical synthesis method in the art (W. H. Freeman and Co., Proteins; structures and molecular principles, 1983). Particularly, the peptide can be synthesized by solution phase peptide synthesis, solid-phase peptide syntheses, fragment condensation, and F-moc or T-BOC chemical method, and more particularly, it can be synthesized by solid-phase peptide synthesis.

The peptide of the present invention can also be prepared by the following genetic engineering method. First, a DNA sequence encoding the peptide is constructed according to the conventional method. The DNA sequence can be prepared by PCR amplification using appropriate primers. Alternatively, the DNA sequence can be synthesized by the standard method known in the art, such as using automated DNA synthesizers (eg, products of Biosearch or Applied Biosystems).

The DNA sequence is inserted into a vector comprising one or more expression control sequences (eg, promoters, enhancers, etc.) that are operably linked thereto to regulate the DNA sequence expression. The host cell is transformed with the recombinant expression vector formed therefrom, and the resulting transformant is cultured under the appropriate media and conditions to allow the DNA sequence to be expressed. Then, the substantially pure peptide encoded by the DNA sequences is recovered from the culture product using the method known in the art (eg, chromatography). The genetic engineering method for the peptide synthesis of the present invention can be referred to the following literature: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Edition; Gene Expression Technology, Method in Enzymology, Genetics and Molecular Biology, Method in Enzymology, Guthrie & Fink (eds.), Academic Press, San Diego, Calif, 1991; and Hitzeman et al., J. Biol. Chem., 255:12073-12080, 1990.

The toxin protein can be composed of the amino acid sequence represented by SEQ. ID. NO: 15.

The said α3 and α4 can be the residues involved in binding of VapC26 and VapB26. Particularly, in an embodiment of the present invention, a3 can be composed of the $37^{th}$ to $52^{nd}$ amino acid sequence of VapC26. In addition, a4 can be composed of the $54^{th}$ to $65^{th}$ amino acid sequence of VapC26.

The peptide can include a polypeptide consisting of any sequence known in the art. In an embodiment of the present invention, the peptide can be composed of any one or more amino acid sequences selected from the group consisting of SEQ ID NOs: 11~13. More particularly, the peptide can be a peptide consisting of the amino acid sequence represented by SEQ ID NO: 12.

The peptide can be a variant of an amino acid sequence having a different sequence formed by deletion, insertion, substitution, or a combination thereof of amino acid residues within a range that does not affect the function of the protein. Amino acid exchange in proteins or peptides that does not alter the activity of the molecule as a whole is known in the art. In some cases, it can be modified by phosphorylation, sulfation, acrylation, glycosylation, methylation, or farnesylation. Therefore, the present invention can include a polypeptide having an amino acid sequence substantially identical to a polypeptide having an amino acid sequence represented by any one or more sequences selected from the group consisting of SEQ ID NOs: 11~13, and a variant or a fragment thereof. The said substantially identical polypeptide can have homology with at least 80%, specifically at least 90% and more specifically at least 95% with the polypeptide of the present invention. In addition, the peptide does not affect the activity of the toxin.

In a preferred embodiment of the present invention, the present inventors identified the structure of VapBC26 to synthesize an antibiotic peptide that can inhibit toxin-antitoxin binding. To do so, the VapBC26 protein complex, toxin (VapC26) and antitoxin (VapB26) proteins of *Mycobacterium tuberculosis* were isolated and purified. Then, the molecular weight of the VapBC26 protein complex was confirmed almost similar to the theoretical molecular weight of the VapBC26 hetero-octamer model by performing the experiments such as multi-angle light scattering and sitting-drop vapor diffusion, and the specific structure was determined (see FIGS. 1~7).

According to the structure confirmed above, seven peptides were designed that mimic the binding region of the toxin without affecting the toxin. When they were treated with the VapBC26 protein complex, the formation of the protein complex was inhibited (see FIGS. 9 and 10). By further experiments, it was confirmed that the Tyr51 region of VapB26 played the most important role in the interaction between VapB26 and VapC26 (see FIG. 9).

Thus, the synthetic peptide of the present invention inhibited the formation of a toxin-antitoxin protein complex of *Mycobacterium tuberculosis* without affecting the activity of the toxin, thereby inducing the death of *Mycobacterium tuberculosis* by means of a separated toxin. Therefore, the synthetic peptide can be effectively used as an antibiotic peptide against *Mycobacterium tuberculosis*.

The present invention also provides an antibiotic composition against *Mycobacterium tuberculosis* comprising the antibiotic peptide as an active ingredient.

The antibiotic composition against *Mycobacterium tuberculosis* can inhibit any one or more residues selected from the group consisting of a3 and a4 of a *Mycobacterium tuberculosis* toxin protein from binding to an antitoxin protein. Therefore, it is possible to suppress the formation of the VapBC26 complex, which is a conjugate of toxin-antitoxin of *Mycobacterium tuberculosis*.

The toxin protein can be composed of the amino acid sequence represented by SEQ ID NO: 15. The α3 and a4 can be the residues involved in binding of VapC26 and VapB26. Particularly, in an embodiment of the present invention, a3 can be composed of the $37^{th}$ to $52^{nd}$ amino acid sequence of VapC26. In addition, a4 can be composed of the $54^{th}$ to $65^{th}$ amino acid sequence of VapC26.

The peptide can include a polypeptide consisting of any sequence known in the art. In an embodiment of the present invention, the peptide can be composed of any one or more amino acid sequences selected from the group consisting of SEQ ID NOs: 11~13. More particularly, the peptide can be a peptide consisting of the amino acid sequence represented by SEQ ID NO: 12.

The peptide can be a variant of an amino acid sequence having a different sequence formed by deletion, insertion, substitution, or a combination thereof of amino acid residues within a range that does not affect the function of the protein. Amino acid exchange in proteins or peptides that does not alter the activity of the molecule as a whole is known in the art. In some cases, it can be modified by phosphorylation, sulfation, acrylation, glycosylation, methylation, or farnesylation. Therefore, the present invention can include a polypeptide having an amino acid sequence substantially identical to a polypeptide having an amino acid sequence represented by any one or more sequences selected from the group consisting of SEQ ID NOs: 11~13, and a variant or a fragment thereof. The said substantially identical polypeptide can have homology with at least 80%, specifically at least 90% and more specifically at least 95% with the polypeptide of the present invention. In addition, the peptide does not affect the activity of the toxin.

The synthetic peptide of the present invention inhibits the formation of a toxin-antitoxin complex of *Mycobacterium tuberculosis* without affecting the activity of the toxin (see FIGS. 9 and 10), thereby inducing the death of *Mycobacterium tuberculosis* by means of the separated toxin. Therefore, the peptide can be effectively used as an antibiotic composition against *Mycobacterium tuberculosis*.

The antibiotic composition comprising the antibiotic peptide of the present invention preferably contains the antibiotic peptide at the amount of 0.1 to 50 weight % by the total weight of the composition, but not always limited thereto.

The composition of the present invention can further include suitable carriers, excipients and diluents commonly used in the preparation of a medicine.

The composition of the present invention can be formulated for oral administration, for example powders, granules, tablets, capsules, suspensions, emulsions, syrups and aerosols, and for parenteral administration, for example external use, suppositories and sterile injections, etc. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. Formulations can be prepared by using generally used excipients or diluents such as fillers, extenders, binders, wetting agents, disintegrating agents and surfactant. Solid formulations for oral administration are tablets, pills, powders, granules and capsules. These solid formulations are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The present invention also provides an antibiotic quasi-drug against *Mycobacterium tuberculosis* comprising the antibiotic peptide as an active ingredient.

The antibiotic quasi-drug against *Mycobacterium tuberculosis* can inhibit any one or more residues selected from the group consisting of a3 and a4 of a *Mycobacterium tuberculosis* toxin protein from binding to an antitoxin protein. Therefore, it is possible to suppress the formation of the VapBC26 complex, which is a conjugate of toxin-antitoxin of *Mycobacterium tuberculosis*.

The toxin protein can be composed of the amino acid sequence represented by SEQ ID NO: 15. The α3 and a4 can be the residues involved in binding of VapC26 and VapB26. Particularly, in an embodiment of the present invention, a3 can be composed of the $37^{th}$ to $52^{nd}$ amino acid sequence of VapC26. In addition, a4 can be composed of the $54^{th}$ to $65^{th}$ amino acid sequence of VapC26. The peptide does not affect the activity of the toxin.

The synthetic peptide of the present invention inhibits the formation of a toxin-antitoxin protein complex of *Mycobacterium tuberculosis* without affecting the activity of the toxin (see FIGS. 9 and 10), thereby inducing the death of *Mycobacterium tuberculosis* by means of the separated toxin. Therefore, the synthetic peptide can be effectively used as an antibiotic quasi-drug against *Mycobacterium tuberculosis*.

When the composition of the present invention is used as a quasi-drug additive, the peptide can be added as it is, or used together with other quasi-drugs or quasi-drug components, and can be appropriately used according to the conventional method. The mixing amount of the active ingredient can be appropriately determined according to the purpose of use.

The quasi-drug composition of the present invention is preferably disinfectant cleaner, shower foam, gagreen, wet tissue, detergent soap, hand wash, humidifier filler, mask, ointment, patch or filter filler, but not always limited thereto.

The present invention also provides an antibiotic external preparation against *Mycobacterium tuberculosis* comprising the antibiotic peptide as an active ingredient.

The antibiotic external preparation against *Mycobacterium tuberculosis* can inhibit any one or more residues selected from the group consisting of α3 and α4 of a *Mycobacterium tuberculosis* toxin protein from binding to an antitoxin protein. Therefore, it is possible to suppress the formation of the VapBC26 complex, which is a conjugate of toxin-antitoxin of *Mycobacterium tuberculosis*.

The toxin protein can be composed of the amino acid sequence represented by SEQ ID NO: 15. The α3 and α4 can be the residues involved in binding of VapC26 and VapB26. Particularly, in an embodiment of the present invention, a3 can be composed of the 37$^{th}$ to 52$^{nd}$ amino acid sequence of VapC26. In addition, a4 can be composed of the 54$^{th}$ to 65$^{th}$ amino acid sequence of VapC26. The peptide does not affect the activity of the toxin.

The synthetic peptide of the present invention inhibits the formation of a toxin-antitoxin protein complex of *Mycobacterium tuberculosis* without affecting the activity of the toxin (see FIGS. 9 and 10), thereby inducing the death of *Mycobacterium tuberculosis* by means of the separated toxin. Therefore, the synthetic peptide can be effectively used as an antibiotic external preparation against *Mycobacterium tuberculosis*.

The present invention also provides a method for preventing, ameliorating or treating *Mycobacterium tuberculosis* comprising a step of administering the antibiotic peptide to a subject.

The antibiotic peptide of the present invention can have the characteristics as described above. The subject may be a mammal, specifically a human.

The composition of the present invention can be administered orally or parenterally, and any parenteral administration can be used. At this time, systemic or topical administration is possible, but systemic administration is more preferred, and intravenous administration is most preferred.

The effective dosage of the composition of the present invention can be determined according to condition and weight of a patient, severity of a disease, form of a drug, administration pathway and duration by those skilled in the art. However, for the desired effect, the effective dosage of the antibiotic peptide of the present invention is 1-2 mg/kg, preferably 0.5-1 mg/kg, and can be administered 1 to 3 times a day.

The antibiotic composition of the present invention can be administered to a patient in the form of bolus, by single dose having relatively short period of infusion or by multiple dose of fractionated treatment protocol for a long term.

In addition, the present invention provides a use of the antibiotic peptide for the preparation of antibiotics against *Mycobacterium tuberculosis*.

The antibiotic peptide of the present invention can have the characteristics as described above.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Expression and Purification of Toxin (VapC26) and Antitoxin (VapB26) Protein The present inventors performed the following process to obtain *Mycobacterium tuberculosis* toxin (VapC26), antitoxin (VapB26) and a toxin-antitoxin (VapBC26) protein complex.

<1-1> Cloning and Transformation of Toxin and Antitoxin Genes

First, the gene Rv0582 (Bioneer Innovation, Korea) encoding the toxin protein VapC26 of *Mycobacterium tuberculosis* and the gene Rv0581 (Bioneer Innovation, Korea) encoding the antitoxin protein VapB26 were amplified by PCR (polymerase chain reaction). The sequence of each primer used for PCR is as follows.

TABLE 1

| Gene | Primer | SEQ. ID. NO: |
|---|---|---|
| VapC26 | 5'-GGAA TTC CAT ATG ATC GAC ACG AGT GCG-3' (forward) | SEQ. ID. NO: 1 |
| | 5'-CCG CTC GAG TTA CGG AAT GAC GGT GAA CGC CCC-3' (reverse) | SEQ. ID. NO: 2 |
| VapB26 | 5'-G AAT TCC AT ATG GAC AAG ACG ACG GTC-3' (forward) | SEQ. ID. NO: 3 |
| | 5'-TTA CCG CTC GAG CCG CTC ACCGAAGCCAGC CAG-3' (reverse) | SEQ. ID. NO: 4 |
| VapB26 (for mutation) | 5'-GGCGGGGCCTGGGAGATGGCCAACTGCG GTGCC-3' (forward) | SEQ. ID. NO: 5 |
| | 5'-GGCACCGCAGTTGGCCATCTCCCAGGCC CCGCC-3' (reverse) | SEQ. ID. NO: 6 |

VapC26 was obtained by performing size exclusion chromatography using HiLoad 16/60 Superdex 75 prep-grade column (GE Healthcare) under the same buffer condition as used in the purification of apBC26.

<Example 2> Multi-Angle Light Scattering Combined with Size Exclusion Chromatography Multi-angle light scattering (MALS) was performed to determine the oligomer structures of VapB26 and VapBC26.

Size exclusion chromatography was performed by using 1260 Infinity HPLC system (Agilent Technologies) with BioSep SEC-s3000 column (Phenomenex). Scattering data were obtained from the miniDAWN-TREOS line (Wyatt Technology) at 657.4 nm for emission and analyzed with ASTRA 6.0.1.10 software (Wyatt Technology). For the experiment, 100 μM of VapB26 and VapBC26 were used. VapB26 was analyzed in a buffer containing 20 mM MES (pH 6) and 50 mM NaCl, which was the condition of NMR experiment, and VapBC26 was analyzed in a buffer containing 50 mM Tris-HCl (pH 7.9), 500 mM NaCl and 250 mM imidazole, which was the condition of protein crystallization experiment. All experiments were performed at room temperature.

Figure 1B:
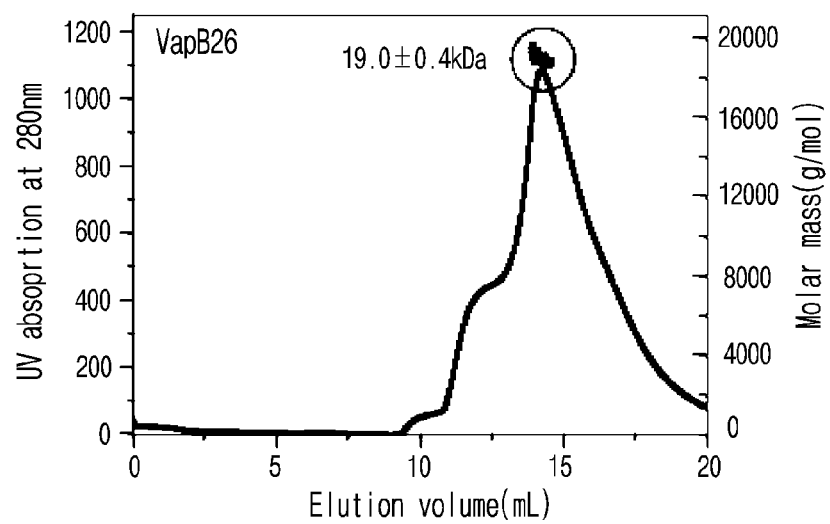
Figure 2A:
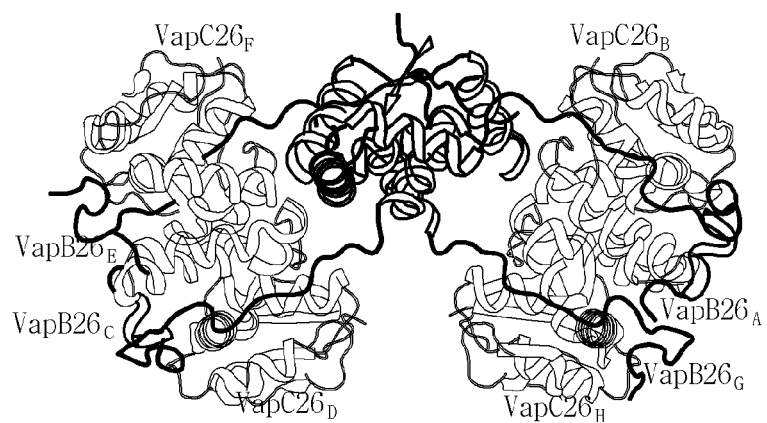
FIGS. 2a to 2d are schematic diagrams showing the structure of the VapBC26 complex.
Figure 2B:
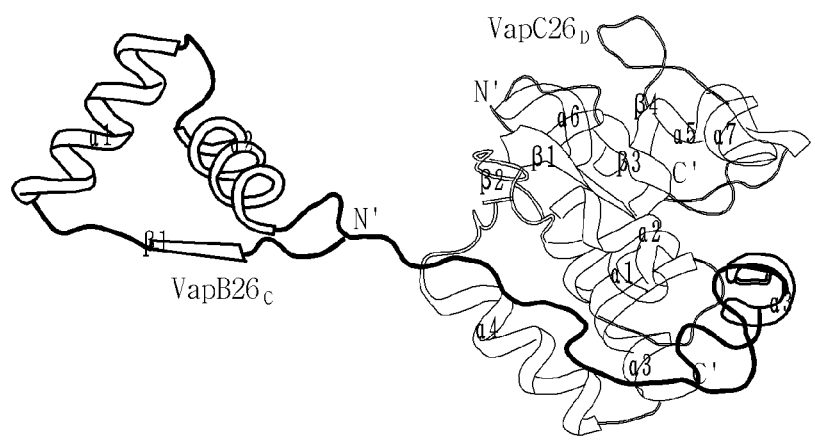
Figure 2C:
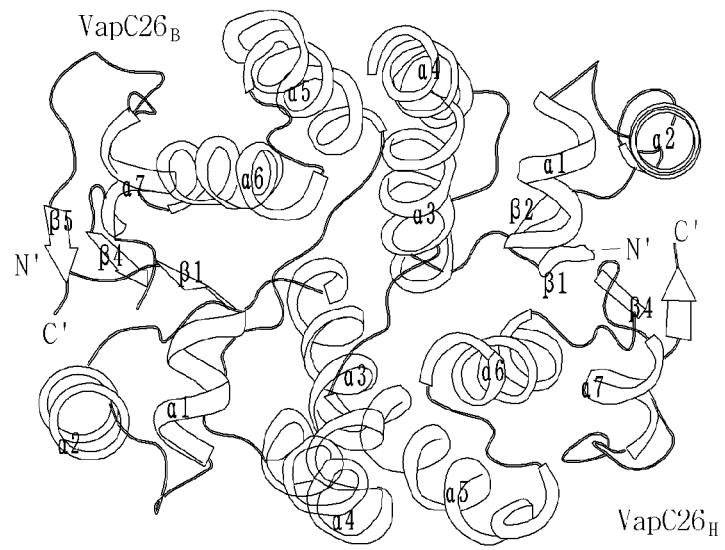
Figure 2D:
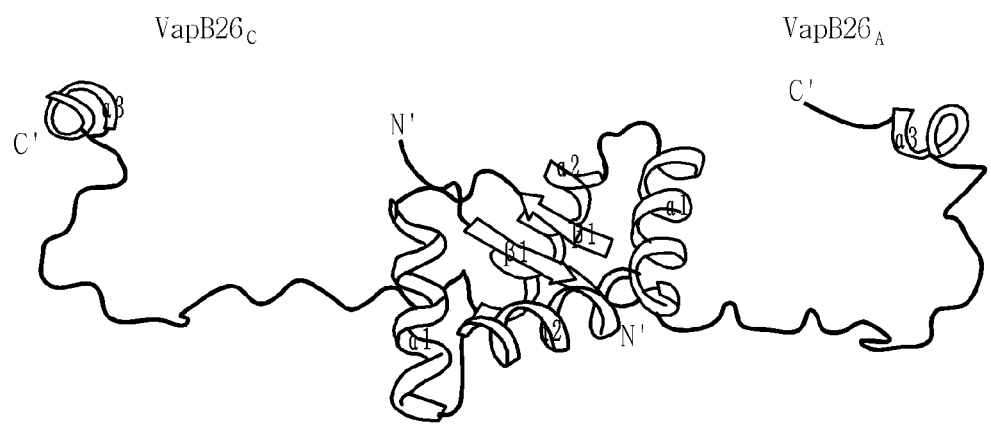
Figure 3A:
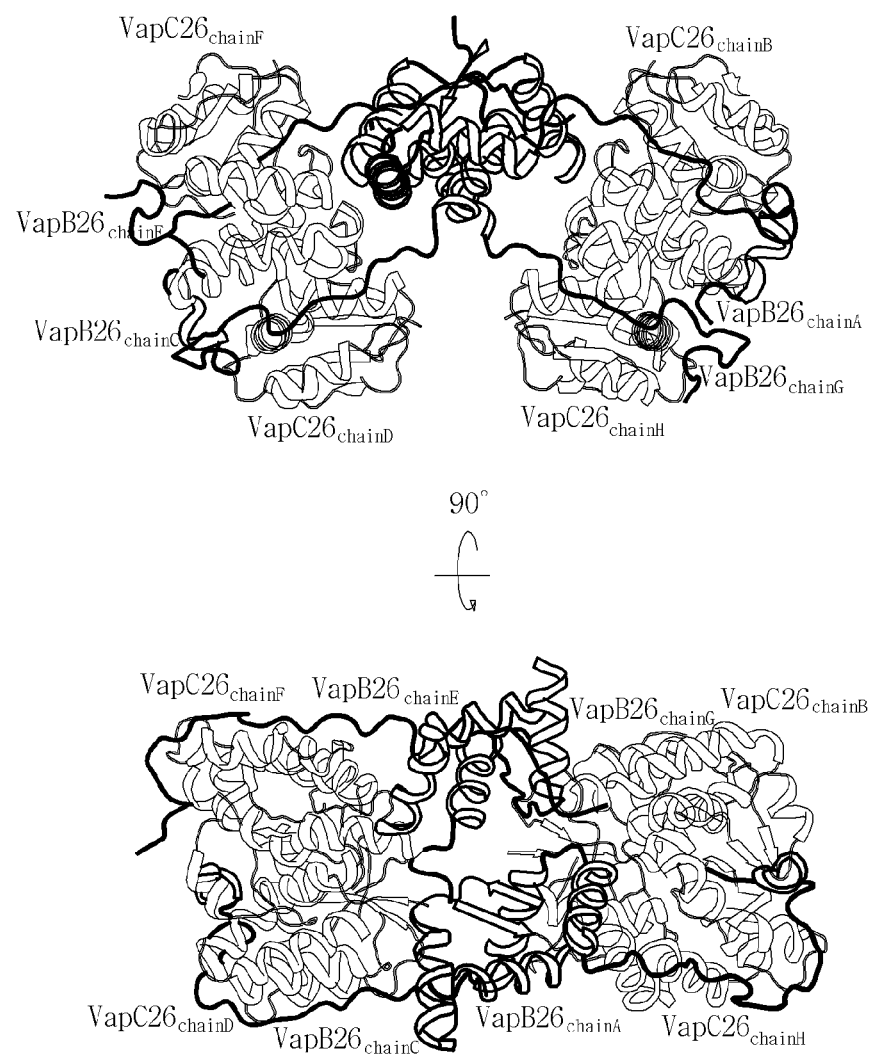
FIGS. 3a to 3d are diagrams showing the shapes of VapBC26 hetero-octamer, VapC26 dimer, VapB26 dimer and VapBC26 hetero-dimer from various aspects.
Figure 3B:
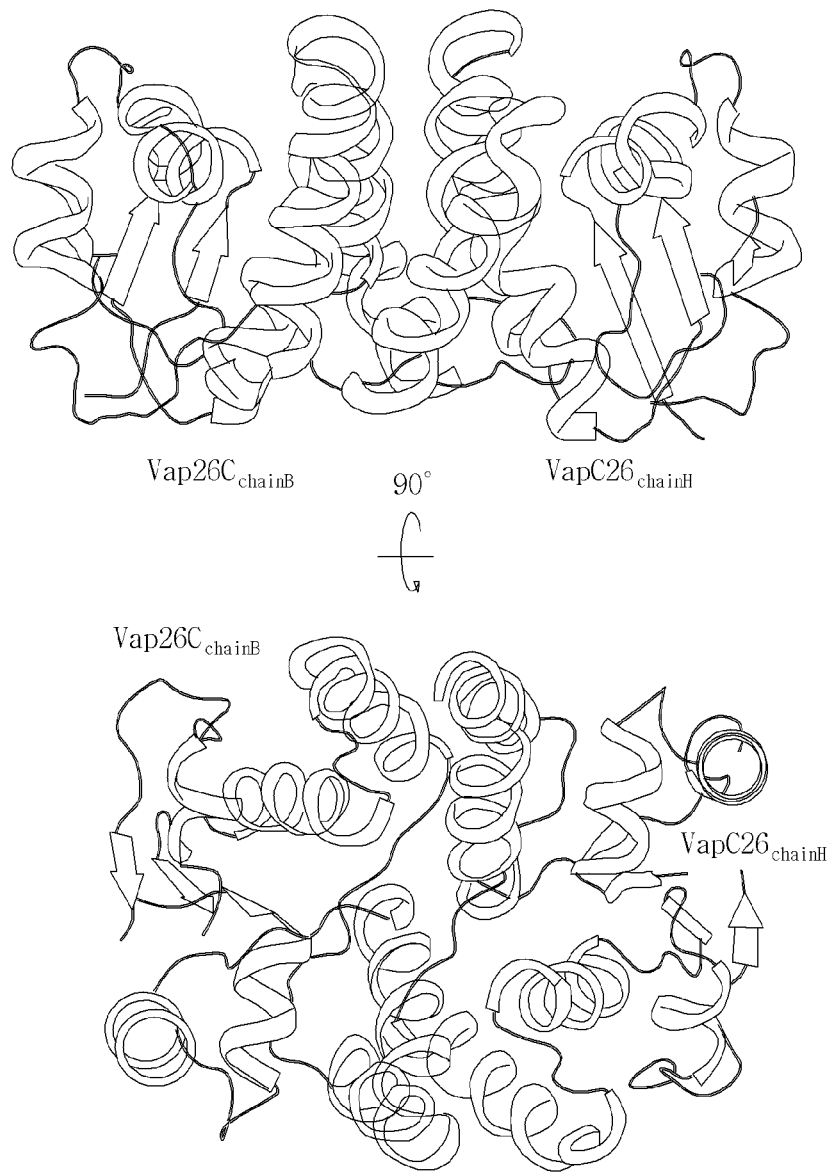
Figure 3C:
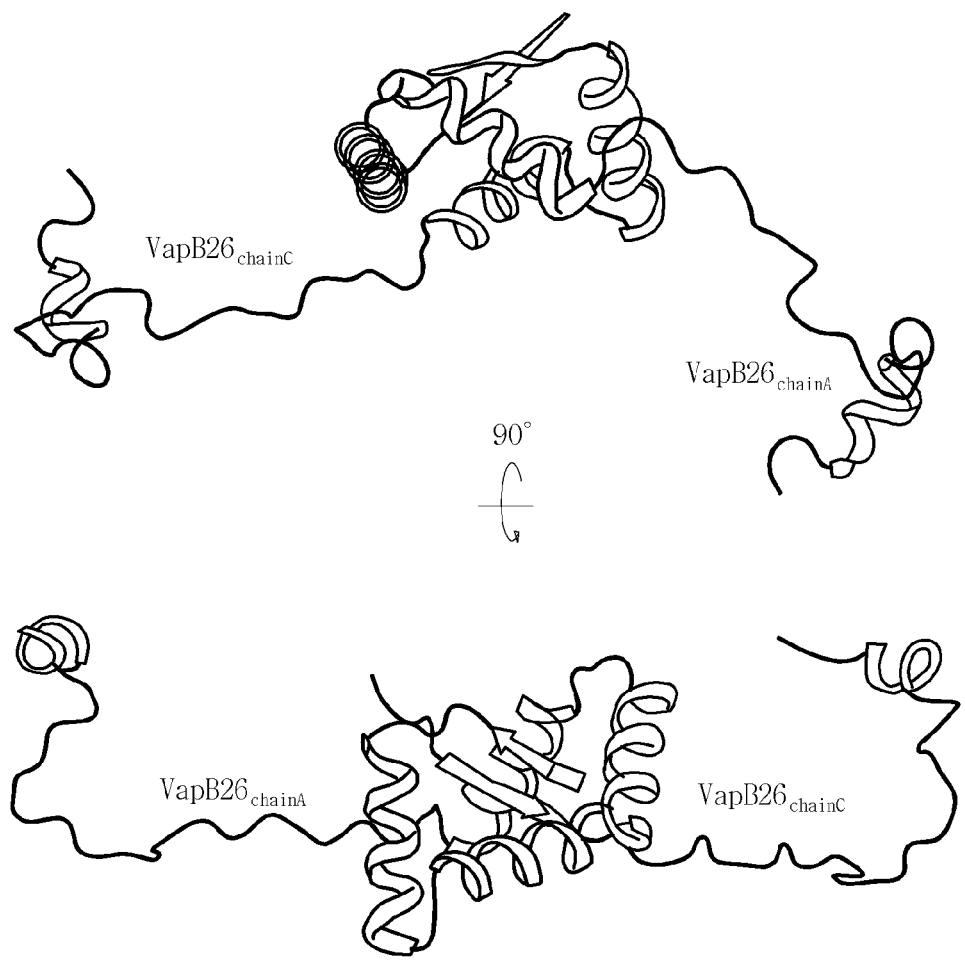
Figure 3D:
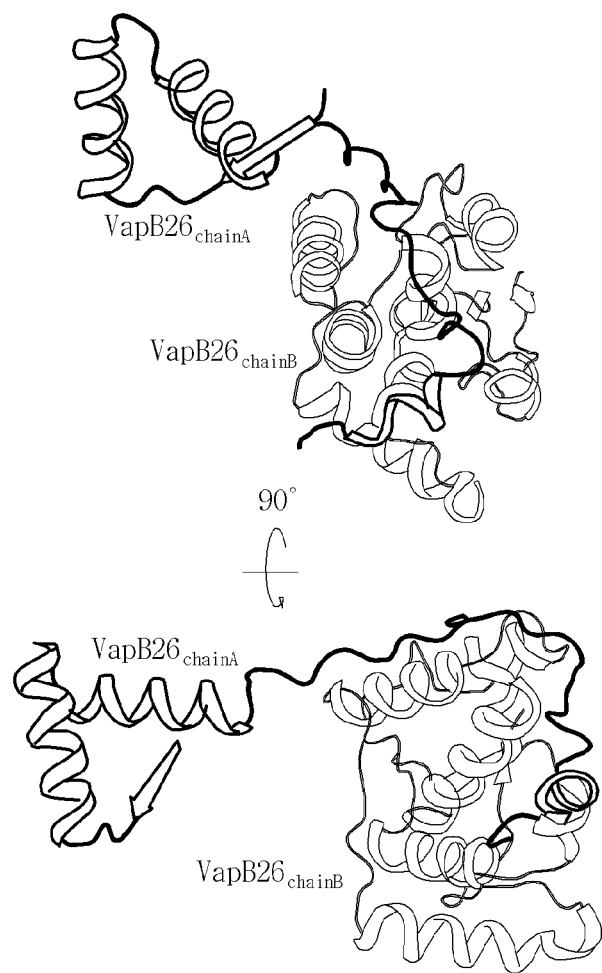

As a result, as shown in FIGS. 1a and 1b, it was confirmed that the molecular weight of the VapBC26 protein complex was 97.5±1.6 kDa, which was almost similar to the theoretical molecular weight (97.0 kDa) of the hetero-octamer model of VapBC26 (FIGS. 1a and 1b).

<Example 3> Structural Analysis of Toxin and Antitoxin Proteins

<3-1> Formation of Toxin-Antitoxin (VapBC26) Protein Complex Crystal and Data Analysis Sitting-drop vapor diffusion was performed to confirm the crystal structure of the VapBC26 protein complex purified in Example 1.

Samples were prepared by mixing 1 μl of the VapBC26 protein complex solution dissolved in 50 mM Tris-HCl at the concentration of 5 mg/ml with 250 mM imidazole containing 1 μl of reservoir solution. Initial crystal screening with the VapBC26 protein complex was performed using crystal screening 1, 2 and Index 1, 2 kit (Hamton Research).

Crystals of the VapBC26 complex were grown at 4° C., and 25% Taximate (pH 7.0) was used as a crystallization solution. The crystals were frozen immediately with liquid nitrogen because severe cracking damage occurred when they were contacted with glycerol containing a cryoprotectant.

Data were collected using beamline 7A and ADSC Quantum Q270 CCD detector in Pohang Accelerator Center (Korea). As a result, as shown in Table 2, the unit cell parameters of the crystals of the native VapBC26 complex were as follows: a=64.35 Å, b=64.35 Å, c=216.96 Å and α=β=γ=90°. The unit cell parameters of the crystals of the VapBC26 substituted with selenomethionine (SeMet) were as follows: a=64.22 Å, b=64.22 Å, c=216.13 Å and α=β=γ=90°. Both proteins belonged to the square space group P41. On the other hand, the calculated total mass of the protein complex containing His-6 tag at N terminus was 24,116.3 Da. At this time, all data were processed using HKL2000 software. The structure of the VapBC26 complex of *Mycobacterium tuberculosis* was analyzed at 2.65 Å resolution by single wavelength anomalous dispersion using SeMet (2.55 Å to the native complex crystals) (Table 2a).

In addition, the mutation of Met50 did not affect the folding of the protein, the structures of the two complexes were almost the same, and the pattern of protein-protein interaction was also the same (Table 2b). The native complex crystals showed slightly better resolution. However, the selenomethionine-substituted crystals were analyzed as with the native complex, and the crystallization conditions and spatial groups were the same, so further analysis was performed using the data of SeMet.

TABLE 2

(a) Data Collection

| Data Collection | Se-Met | Native |
|---|---|---|
| X-ray source | 7A beamline of PLS | 7A beamline of PLS |
| X-ray wavelength (Å) | 0.9794 | 0.9795 |
| Space group | P4$_1$ | P4$_1$ |
| Unit cell parameters/a, b, c (Å) | 64.22, 64.22, 216.13 | 64.35, 64.35, 216.96 |
| Unit cell parameters α, β, γ (°) | c = 233.03 | c = 232.79 |
| Resolution range (Å) | 30-2.65 | 50-2.65 |
| molecules per ASU | 4 VapBC26 heterodimers | 4 VapBC26 heterodimers |
| observed reflections(>1σ) | 619653 | 105433 |
| unique reflections | 25229 | 27340 |
| Completeness(%) | 99.8 (100) $^e$ | 94.9 (99.1) $^e$ |
| <I/σ(I)> | 70.20 (10.87) $^e$ | 34.98 (3.93) $^e$ |
| multiplicity$^a$ | 24.6 (25.4) $^e$ | 3.9 (4.2) $^e$ |
| R$_{merge}$$^b$ | 11.3 (54.3) $^e$ | 7.8 (67) $^e$ |

(b) Additional Analysis

| | | |
|---|---|---|
| R$_{work}$$^c$ | 20.8 | 22.8 |
| R$_{free}$$^d$ | 23.9 | 28.4 |

No. of atoms/average B-factor (Å$^2$)

| | | |
|---|---|---|
| Protein | 6170/61.0 | 5978/79.8 |
| Water oxygen | 65/47.9 | 54/83.1 |

RMSD$^f$ from ideal geometry

| | | |
|---|---|---|
| Bond distance (Å) | 0.006 | 0.007 |
| Bond angle (°) | 1.25 | 1.27 |

TABLE 2-continued (a) Data Collection

| Data Collection | Se-Met | Native |
|---|---|---|

Ramachandran statistics

| | | |
|---|---|---|
| Most favored regions (%) | 96.2 | 95.5 |
| Additional allowed regions (%) | 3.7 | 4.4 |
| Residues in disallowed regions (%) | 0.1 | 0.1 |

$^a$N$_{obs}$/Nu$_{nique}$
$^b$R$_{merge}$ = Σ (I − <I>) I Σ<1>
$^c$R$_{work}$ = Σ$_{hkl}$||F$_{obs}$| − k|F$_{calc}$||/Σ$_{hkl}$|F$_{obs}$|
$^d$R$_{work}$ value was calculated at reflection.
$^e$The value in the insert is the highest resolution shell value.
$^f$RMSD (Root mean square deviation) was obtained using REFMAC ™.

<3-2> Confirmation of Toxin-Antitoxin (VapBC26) Protein Complex Structure

The crystal structure of the VapBC26 protein complex of *Mycobacterium tuberculosis* was confirmed based on the data obtained in Example <3-1>.

The asymmetric unit of the VapBC26 protein complex crystal included four VapB26 and four VapC26 proteins in a hetero-octameric assembly. Four of the heterodimeric VapBC26 protein complexes were included in the asymmetric unit. A VapB26 dimer was bound to two VapC26 monomers, and the two VapB$_2$C$_2$ complexes were linked to each other by a double axis. A flexible hinge loop of the antitoxin was confirmed to envelope the toxin protein by a hook known as the looped arm shape (FIGS. 2a~2d and FIGS. 3a~3d).

<3-3> Confirmation of Toxin (VapC26) Protein Structure

The structure of VapC26, a toxin protein of *Mycobacterium tuberculosis*, was confirmed based on the data obtained in Example <3-1>.

As a result, it was confirmed that VapC26 contained 7 α-helices and 5 β-helices. In addition, as shown in FIG. 3, it was composed of the α/β/α sandwich folded shape consisting of β3-helices and 7 α-helices: β1 (residues 1-4), α1 (residues 5-13), α2 (residues 18-27), β2 (residues 33-36), α3 (residues 37-52), α4 (residues 54-65), β3 (residues 68-71), α5 (residues 74-92), α6 (residues 94-108), β4 (residues 110-114), α7 (residues 116-124) and β5 (residues 129-134) (FIG. 3). On the other hand, four-stranded parallel sheets (β2-β1-β4-β5) were surrounded by 5 α-helices with two remaining α-helices (α3 and α4) located outward of the structure.

<3-4> Confirmation of Antitoxin (VapB26) Protein Structure

The structure of VapB26, an antitoxin protein of *Mycobacterium tuberculosis*, was confirmed based on the data obtained in Example <3-1>.

As a result, it was confirmed that VapB26 contained 3 α-helices and one β-strand having β1-α1-β2-β3 status. The four secondary structural elements corresponded to residues 3-6 (β1), residues 10-23 (α1), residues 27-39 (α2) and residues 60-65 (α3) of chain A, and to residues 4-7 (β1), residues 10-23 (α1), residues 27-39 (α2) and residues 60-65 (α3) of chain C. The structure of VapB26 was characterized by an N-terminal sheet, two adjacent helices and a small C-terminal α-helix with a long hinge loop between α2- and β3-helices (FIGS. 3a~3d). Three consecutive prolines (Pro44, Pro45 and Pro46) were located between α2-helix and the long loop. On the other hand, Gly24 located in the short loop region between α1- and α2-helices generated a turn shape by forming hydrogen bonds with the adjacent residues.

In addition, two VapB26 dimers interacted with each other through the N-terminal β-strand to form a homodimer. The calculated molecular weight of VapB26 was 19.0±0.4 kDa, which was almost same to the theoretical molecular weight of the VapB26 dimer (19.2 kDa) (FIGS. 1a and 1b). The N-terminal domain of the dimer had the RHH motif and the dimer interface showed an average area of about 1372.3 Å$^2$ (1332.2 Å$^2$ between chains E and G; and 1412.4 Å$^2$ between chains A and C). More than 30 residues of each VapB26 were involved in dimerization, and the most notable difference between the two VapB26 structures was observed in the N-terminal domain. In addition, the N-terminal domains of the chains A and C were structurally well aligned, but the N-terminal domains of the chains E and G were not well folded.

<Example 4> Analysis of Characteristics of Toxin-Antitoxin (VapBC26) Protein Complex To analyze the structural similarity of the VapBC26 protein complex, structural homologs of VapBC26 were screened using DALI server, a three-dimensional mapping program, to identify the structural differences between the VapBC26 protein complex and VapB5, VapB15 and VapB30.

Figure 4A:
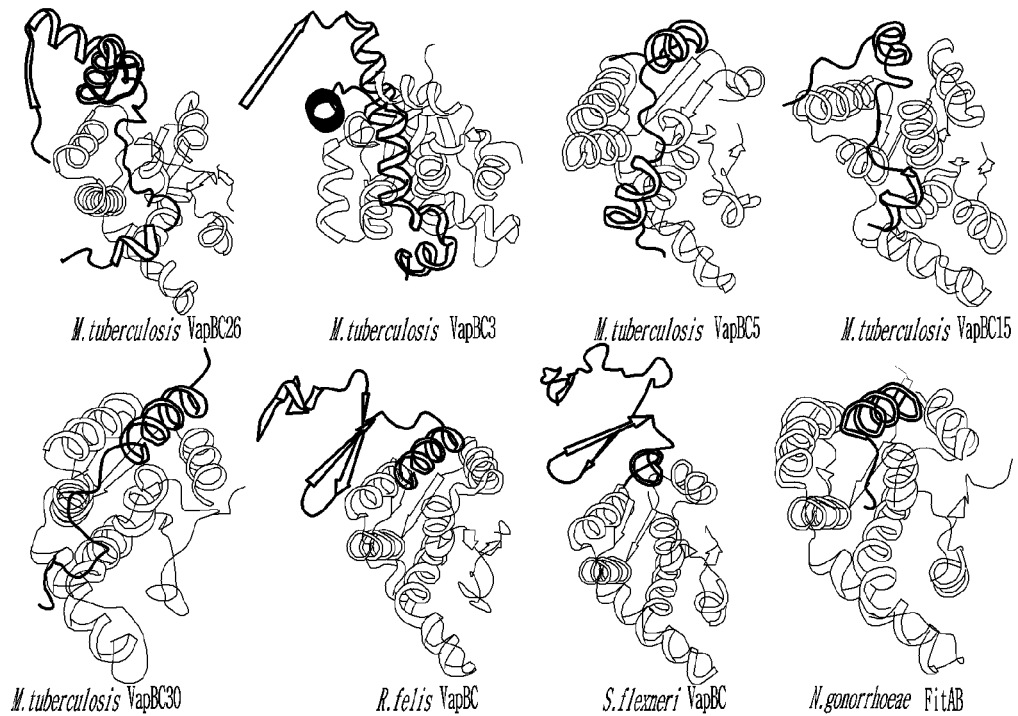
FIGS. 4a and 4b are diagrams showing the structures of the VapBC26 complex and VapB proteins compared to their homologs.
Figure 4B:
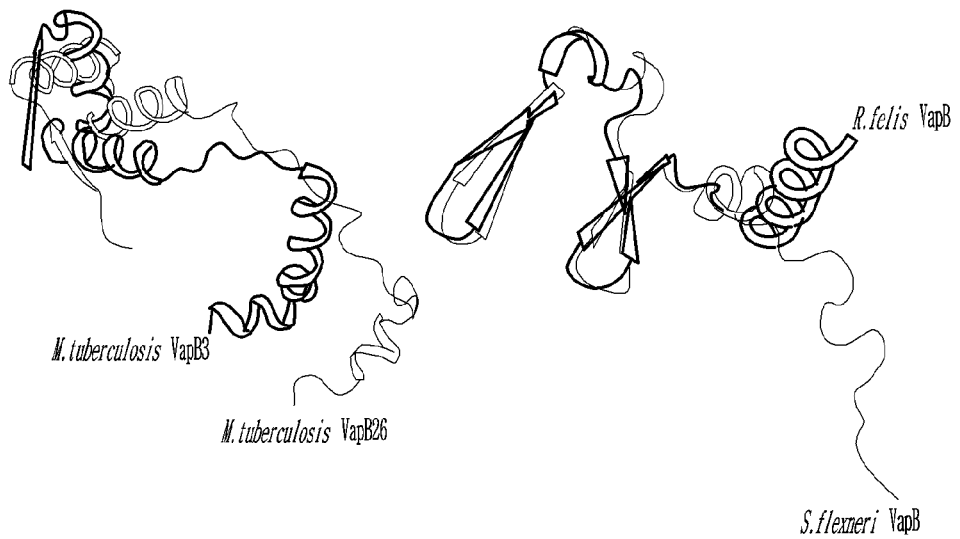

As a result, in the structural homologs, it was confirmed that the binding region of the toxin to the antitoxin was mainly composed of one or two α-helices, but the binding region of the antitoxin to the toxin was composed of α-helix and four antiparallel β sheets. In addition, the structures of VapB5, VapB15 and VapB30 included only one α-helix (VapB30) or two α-helices (VapB5 and VapB15). The VapBs protein of *Shigella flexneri* and *Rickettsia felis* strains contained only one α-helix (α2) in the binding region of the toxin. VapB3 of *Mycobacterium tuberculosis* showed a complete electron density map at the N-terminus due to the presence of the elongated α-helix (α3), but VapB26 did not contain specific helices in the binding region, except for the short α-helix at the C-terminus (α3) of chains A and C. VapB26 formed a flexible hinge loop without secondary structure in the binding groove formed by α-helix of VapC26 (FIG. 4a). Interestingly, VapB26 did not share the important structural similarities with other VapB proteins except VapB3. The VapB protein did not have the same DNA binding domain, so only a few VapB proteins with the structures similar to VapB26 were determined to be complete. In addition, DNA binding domains of other VapB proteins were generally located in the N-terminal region, but VapB5, VapB15 and VapB30 of *Mycobacterium tuberculosis* did not have the N-terminal structure, so that the structure of the DNA binding site of these proteins could not be confirmed. Among the VapB proteins whose structures were determined, only VapB3 of *Mycobacterium tuberculosis* shared the same RHH DNA binding site as VapB26. However, in general, VapBC3 of *Mycobacterium tuberculosis* did not have high structural similarity to VapBC26, and the structural similarity was observed only between the antitoxin VapB proteins (FIG. 4b).

<Experimental Example 1> Changes in Ribonuclease Activity of Toxin Protein by Addition of Peptide Imitating Binding Region The following experiment was performed in order to investigate the changes in ribonuclease (RNAse) activity by the peptides imitating the binding regions of VapB26 and toxin VapC26.

First, 7 short peptides were designed to imitate the binding regions of VapB26 and VapC26 and their sequences are shown in Table 3 below. Among these peptides, the peptides consisting of the amino acid sequences represented by SEQ. ID. NOs: 8 and 9 were designed to imitate the binding region of VapB26, and the peptides consisting of the amino acid sequences represented by SEQ. ID. NOs: 10, 11, 12 and 13 were designed to imitate the binding region of VapC26. Then, by adding these peptides to the complex, it was confirmed whether the formation of the toxin-antitoxin protein complex was inhibited. When the peptide binds to the complex with high affinity, the activity of VapC26 isolated from the complex becomes more prevalent, and thereby the ribonuclease activity increases, which can be monitored by fluorescence quenching.

TABLE 3

| Protein | Amino acid sequence | SEQ. ID NO: |
|---|---|---|
| Mimetic peptide for VapB26 Coil between α2 and α3 | PPPRGGLYAGSEPIA(44-58) | SEQ. ID. NO: 8 |
| Mimetic peptide for VapB26 α3 | VDELLAGF(61-68) | SEQ. ID. NO: 9 |
| Mimetic peptide for VapC26 α1 | ALLAYFDAAEP(7-17) | SEQ. ID. NO: 10 |
| Mimetic peptide for VapC26 α3 | PYVVAELDYLVATRVG(37-52) | SEQ. ID. NO: 11 |
| Mimetic peptide for VapC26 α4 | DAELAVLRELAG(54-65) | SEQ. ID. NO: 12 |
| Mimetic peptide for VapC2 partial motif between α3 and α4 | YLVATRVGVDAELAV(45-59) | SEQ. ID. NO: 13 |
| Mimetic peptide for VapC26 whole α3 and α4 | PYVVAELDYLVATRVGVDAELAVLRELAG(37-65) | SEQ. ID. NO: 14 |
| VapC26 | MIIDTSALLA YFDAAEPDHA AVSECIDSSA DALVVSPYVV AELDYLVATR VGVDAELAVL RELAGGAWEL ANCGAAEIEQ AARIVTKYQD QRIGIADAAN VVLADRYRTR TILTLDRRHF SALRPIGGGR FTVIP | SEQ. ID. NO: 15 |

Figure 5A:
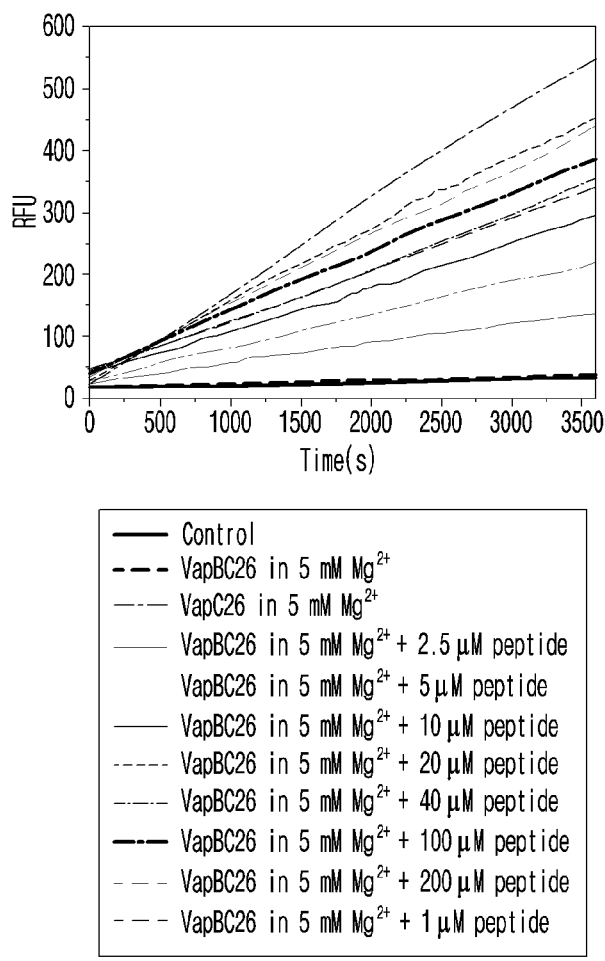
FIGS. 5a to 5d are diagrams showing the ribonuclease activity of VapC26 measured using a mimetic peptide to VapC26 α4 (5a, 5b (mimetic peptide concentration fixation)), the ribonuclease activity measured using the VapBC26 complex and the mutant complex thereof (5c) and the results of size exclusion chromatography performed using the same (5d).
Figure 6:
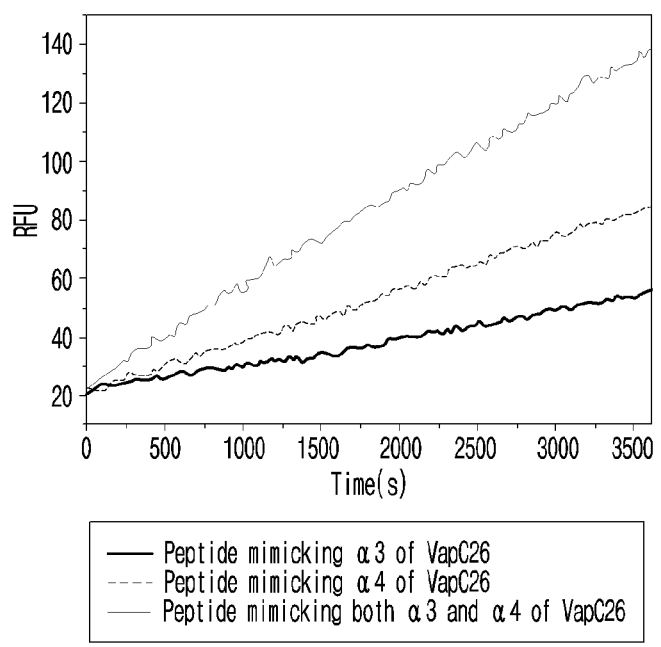
FIG. 6 is a diagram showing the ribonuclease activity of VapBC26 measured when the mimetic peptides a3 and a4 were added respectively or together.

As a result, as shown in FIG. 5a, the ribonuclease activity of the VapBC26 protein complex itself of *Mycobacterium tuberculosis* was weaker than the ribonuclease activity of VapC26 itself. In the presence of 2.5 μM of VapBC26, the ribonuclease activity was increased by competing with the peptide. In addition, the mimetic peptide for VapC26 α3 (SEQ. ID. NO: 11), the mimetic peptide for VapC26 α4 (SEQ. ID. NO: 12) and the mimetic peptide for VapC26 partial motif between α3 and α4 (SEQ. ID. NO: 13) acted as a VapBC26 binding inhibitor (FIGS. 5a and 6). Compared with when the mimetic peptide represented by SEQ. ID. NO:

11 and the mimetic peptide represented by SEQ. ID. NO: 13 were added, the ribonuclease activity of VapBC26 was more increased when the mimetic represented by SEQ. ID. NO: 12 was added (FIG. 6).

Figure 5B:
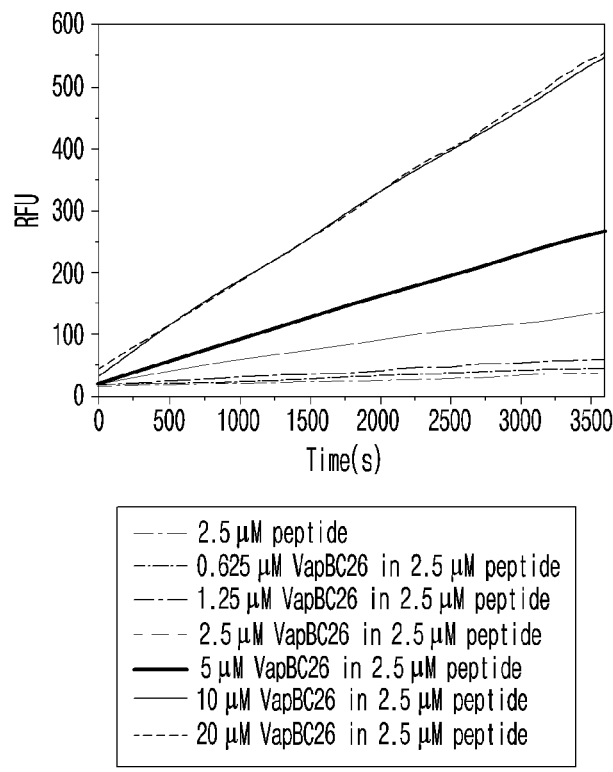

Next, the concentration of the mimetic peptide for VapC26 α4 was fixed at 2.5 μM and the additional experiment was performed with increasing the concentration of VapBC26 from 0.625 to 20 μM. As a result, as shown in FIG. 5b, from the concentration of VapBC26 of 10 μM, the results of RFU were similar (FIG. 5b).

<Experimental Example 2> Changes in Ribonuclease Activity by Mutation

First, mutations were induced in VapB26 using EZchange™ site-directed mutation kit (Enzynomics, Korea) according to the manufacturer's protocol. Through this process, Pro46 and Tyr51 of VapB26 and Leu46 of VapC26 involved in hydrophobic binding were replaced with alanine or glutamate to reduce or eliminate hydrophobicity. Key binding residues were identified by adding 10 μM of the mimetic peptide for VapC26 α4 to the prepared mutations. The sequences of the primers used for inducing the mutations are shown in Table 1 (SEQ. ID. NOs: 5 and 6).

Figure 5C:
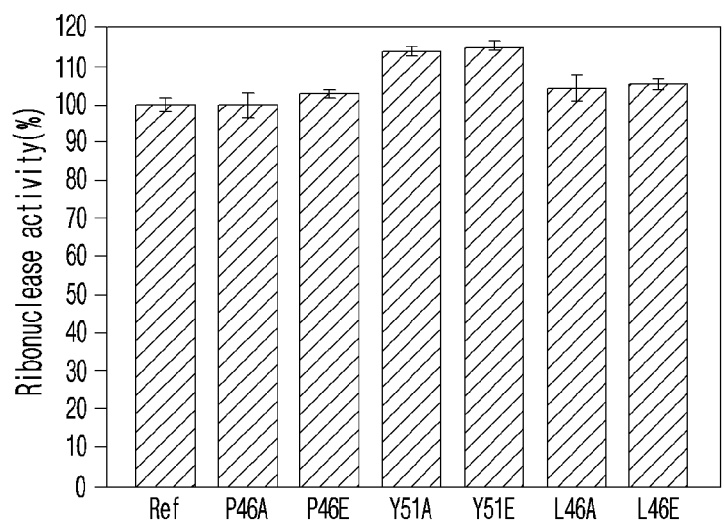

As a result, as shown in FIG. 5c, it was confirmed that Tyr51 of VapB26 played the most important role in the interaction between VapB26 and VapC26 (FIG. 5c).

Figure 5D:
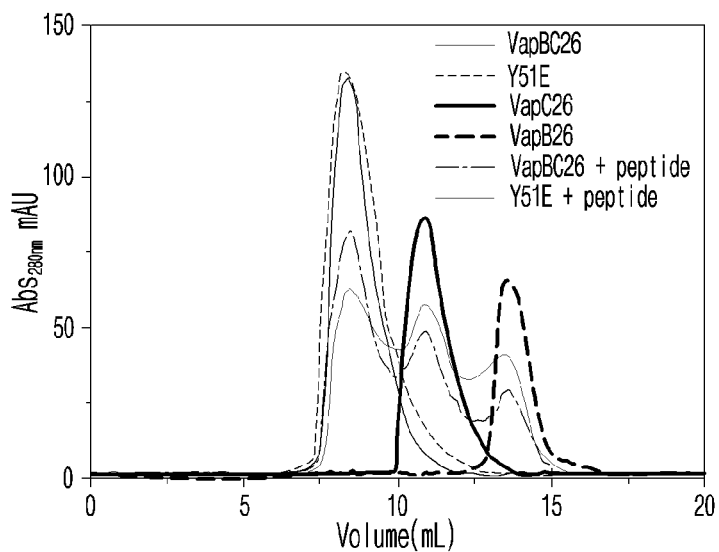

In addition, to support the results above, not only VapB26, VapC26, and the native VapB26 protein complex, but also the VapBC26 protein complex containing Y51E prepared by mutating the 51$^{st}$ Tyr residue of VapB26 with Glu and the VapC26 α4 mimetic peptide supposed to be added to each complex were filled in Superdex 75 10/300 prepacked column (GE Healthcare) with the combinations shown in FIG. 5d, followed by size exclusion chromatography. The results are shown as UV absorbance at 280 nm according to the elution volume.

As a result, as shown in FIG. 5d, the mimic peptides added with the VapBC26 protein complex showed peaks at different positions from the original peaks corresponding to VapB26 and VapC26, and the mimetic peptide added with the protein complex containing Y51E included more degraded proteins compared to the mimetic peptide added with the native protein complex (FIG. 5d). The calculated area corresponding to VapC26 in the mimetic peptide added with the protein complex comprising Y51E was larger by 15.42% than that of the mimetic peptide added with the native protein complex. As shown in FIG. 5c, this is almost consistent with the fluorescence increase of 15.07% in Y51E. Therefore, it was confirmed that Tyr51 of VapB26 played the most important role in the interaction between VapB26 and VapC26 (FIGS. 5c and 5d).

What is claimed is:

1. A method for ameliorating or treating a *Mycobacterium tuberculosis* infection in a subject, comprising:
administering to the subject an effective amount of an antibiotic peptide, wherein the antibiotic peptide consists of the amino acid sequence of SEQ ID NO: 11, SEQ ID NO: 12, or SEQ ID NO: 13,
thereby ameliorating or treating the *Mycobacterium tuberculosis* infection of the subject.

2. The method according to claim 1, wherein the antibiotic peptide consists of SEQ ID NO: 12.

3. The method according to claim 1, wherein the antibiotic peptide inhibits binding of an antitoxin protein of *Mycobacterium tuberculosis* to a toxin protein of *Mycobacterium tuberculosis*.

4. The method according to claim 1, wherein the antibiotic peptide inhibits binding of an antitoxin protein of *Mycobacterium tuberculosis* to a toxin protein of *Mycobacterium tuberculosis*, thereby resulting in death of a cell of *Mycobacterium tuberculosis*.

5. A method for inhibiting binding of an antitoxin protein of *Mycobacterium tuberculosis* to a toxin protein of *Mycobacterium tuberculosis* in a subject, comprising:
administering to the subject an effective amount of an antibiotic peptide consisting of the amino sequence of SEQ ID NOs: 11, SEQ ID NO: 12, or SEQ ID NO: 13,
thereby inhibiting binding of the antitoxin protein of *Mycobacterium tuberculosis* to the toxin protein of *Mycobacterium tuberculosis* in the subject.

6. The method according to claim 5, wherein the antibiotic peptide consists of SEQ ID NO: 12.

7. The method according to claim 5, wherein the administering results in death of a cell of *Mycobacterium tuberculosis*.

* * * * *

SEQUENCE LISTING

```
Sequence total quantity: 21
SEQ ID NO: 1            moltype = DNA  length = 28
FEATURE                 Location/Qualifiers
misc_feature            1..28
                        note = VapC26 F
source                  1..28
                        mol_type = other DNA
                        organism = synthetic construct
SEQUENCE: 1
ggaattccat atgatcgaca cgagtgcg                                     28

SEQ ID NO: 2            moltype = DNA  length = 33
FEATURE                 Location/Qualifiers
misc_feature            1..33
                        note = VapC26 R
source                  1..33
                        mol_type = other DNA
                        organism = synthetic construct
SEQUENCE: 2
ccgctcgagt tacggaatga cggtgaacgc ccc                               33

SEQ ID NO: 3            moltype = DNA  length = 28
FEATURE                 Location/Qualifiers
misc_feature            1..28
                        note = VapB26 F
source                  1..28
                        mol_type = other DNA
                        organism = synthetic construct
SEQUENCE: 3
ggaattccat atggacaaga cgacggtc                                     28

SEQ ID NO: 4            moltype = DNA  length = 33
FEATURE                 Location/Qualifiers
misc_feature            1..33
                        note = VapB26 R
source                  1..33
                        mol_type = other DNA
                        organism = synthetic construct
```

```
SEQUENCE: 4
ttaccgctcg agccgctcac cgaagccagc cag                                        33

SEQ ID NO: 5              moltype = DNA   length = 33
FEATURE                   Location/Qualifiers
misc_feature              1..33
                          note = mutated VapB26 F
source                    1..33
                          mol_type = other DNA
                          organism = synthetic construct
SEQUENCE: 5
ggcggggcct gggagatggc caactgcggt gcc                                        33

SEQ ID NO: 6              moltype = DNA   length = 33
FEATURE                   Location/Qualifiers
misc_feature              1..33
                          note = mutated VapB26 R
source                    1..33
                          mol_type = other DNA
                          organism = synthetic construct
SEQUENCE: 6
ggcaccgcag ttggccatct cccaggcccc gcc                                        33

SEQ ID NO: 7              moltype = AA    length = 19
FEATURE                   Location/Qualifiers
REGION                    1..19
                          note = pET28b N-terminal tag
source                    1..19
                          mol_type = protein
                          organism = synthetic construct
SEQUENCE: 7
MGSSHHHHHS SGLVPRGSH                                                        19

SEQ ID NO: 8              moltype = AA    length = 15
FEATURE                   Location/Qualifiers
REGION                    1..15
                          note = mimicked VapB26 protein coil alpha 2 between alpha 3
source                    1..15
                          mol_type = protein
                          organism = synthetic construct
SEQUENCE: 8
PPPRGGLYAG SEPIA                                                            15

SEQ ID NO: 9              moltype = AA    length = 8
FEATURE                   Location/Qualifiers
REGION                    1..8
                          note = mimicked VapB26 protein alpha 3
source                    1..8
                          mol_type = protein
                          organism = synthetic construct
SEQUENCE: 9
VDELLAGF                                                                    8

SEQ ID NO: 10             moltype = AA    length = 11
FEATURE                   Location/Qualifiers
REGION                    1..11
                          note = mimicked VapC26 protein alpha 1
source                    1..11
                          mol_type = protein
                          organism = synthetic construct
SEQUENCE: 10
ALLAYFDAAE P                                                                11

SEQ ID NO: 11             moltype = AA    length = 16
FEATURE                   Location/Qualifiers
REGION                    1..16
                          note = mimicked VapC26 protein alpha 3
source                    1..16
                          mol_type = protein
                          organism = synthetic construct
```

-continued

```
SEQUENCE: 11
PYVVAELDYL VATRVG                                                  16

SEQ ID NO: 12          moltype = AA  length = 12
FEATURE                Location/Qualifiers
REGION                 1..12
                       note = mimicked VapC26 protein alpha 4
source                 1..12
                       mol_type = protein
                       organism = synthetic construct
SEQUENCE: 12
DAELAVLREL AG                                                      12

SEQ ID NO: 13          moltype = AA  length = 15
FEATURE                Location/Qualifiers
REGION                 1..15
                       note = mimicked VapC26 proteinsome motifs of alpha3 and
                        alpha 4
source                 1..15
                       mol_type = protein
                       organism = synthetic construct
SEQUENCE: 13
YLVATRVGVD AELAV                                                   15

SEQ ID NO: 14          moltype = AA  length = 29
FEATURE                Location/Qualifiers
REGION                 1..29
                       note = mimicked VapC26 proteinwhole alpha3 and alpha 4
source                 1..29
                       mol_type = protein
                       organism = synthetic construct
SEQUENCE: 14
PYVVAELDYL VATRVGVDAE LAVLRELAG                                    29

SEQ ID NO: 15          moltype = AA  length = 135
FEATURE                Location/Qualifiers
REGION                 1..135
                       note = M.tuberculosis VapC26
source                 1..135
                       mol_type = protein
                       organism = synthetic construct
SEQUENCE: 15
MIIDTSALLA YFDAAEPDHA AVSECIDSSA DALVVSPYVV AELDYLVATR VGVDAELAVL  60
RELAGGAWEL ANCGAAEIEQ AARIVTKYQD QRIGIADAAN VVLADRYRTR TILTLDRRHF  120
SALRPIGGGR FTVIP                                                   135

SEQ ID NO: 16          moltype = AA  length = 135
FEATURE                Location/Qualifiers
REGION                 1..135
                       note = M.tuberculosis VapC30
source                 1..135
                       mol_type = protein
                       organism = synthetic construct
SEQUENCE: 16
MIIDTSALLA YFDAAEPDHA AVSECIDSSA DALVVSPYVV AELDYLVATR VGVDAELAVL  60
RELAGGAWEL ANCGAAEIEQ AARIVTKYQD QRIGIADAAN VVLADRYRTR TILTLDRRHF  120
SALRPIGGGR FTVIP                                                   135

SEQ ID NO: 17          moltype = AA  length = 132
FEATURE                Location/Qualifiers
REGION                 1..132
                       note = S.flexneri VapC
source                 1..132
                       mol_type = protein
                       organism = synthetic construct
SEQUENCE: 17
MLKFMLDTNI CIFTIKNKPA SVRERFNLNQ GKMCISSVTL MELIYGAEKS QMPERNLAVI  60
EGFVSRIDVL DYDAAAATHT GQIRAELARQ GRPVGPFDQM IAGHARSRGL IIVTNNTREF  120
ERVGGLRTED WS                                                      132

SEQ ID NO: 18          moltype = AA  length = 132
FEATURE                Location/Qualifiers
REGION                 1..132
                       note = M.tuberculosis VapC15
source                 1..132
                       mol_type = protein
                       organism = synthetic construct
```

```
SEQUENCE: 18
MIVDTSVWIA YLSTSESLAS RWLADRIAAD STVIVPEVVM MELLIGKTDE DTAALRRRLL  60
QRFAIEPLAP VRDAEDAAAI HRRCRRGGDT VRSLIDCQVA AMALRIGVAV AHRDRDYEAI  120
RTHCGLRTEP LF                                                     132

SEQ ID NO: 19           moltype = AA  length = 134
FEATURE                 Location/Qualifiers
REGION                  1..134
                        note = R.felis VapC
source                  1..134
                        mol_type = protein
                        organism = synthetic construct
SEQUENCE: 19
MIYMLDTNIC VYAINKHPDS YYNNLELLAK NNTIAISSIV LAELQYGVSK SKKKEQNQSK  60
LDIFLSRLEI IDFSAKCTFY YGELRTELEQ KGLIIGNNDL LIASHAIAEN ATLVTNNIKE  120
FKRIPNLILE NWDK                                                   134

SEQ ID NO: 20           moltype = AA  length = 141
FEATURE                 Location/Qualifiers
REGION                  1..141
                        note = M.tuberculosis VapC3
source                  1..141
                        mol_type = protein
                        organism = synthetic construct
SEQUENCE: 20
MTDQRWLIDK SALVRLTDSP DMEIWSNRIE RGLVHITGVT RLEVGFSAEC GEIARREFRE  60
PPLSAMPVEY LTPRIEDRAL EVQTLLADRG HHRGPSIPDL LIAATAELSG LTVLHVDKDF  120
DAIAALTGQK TERLTHRPPS A                                           141

SEQ ID NO: 21           moltype = AA  length = 135
FEATURE                 Location/Qualifiers
REGION                  1..135
                        note = M.tuberculosis VapC5
source                  1..135
                        mol_type = protein
                        organism = synthetic construct
SEQUENCE: 21
MSTTPAAGVL DTSVFIATES GRQLDEALIP DRVATTVVTL AELRVGVLAA ATTDIRAQRL  60
ATLESVADME TLPVDDDAAR MWARLRIHLA ESGRRVRIND LWIAAVAASR ALPVITQDDD  120
FAALDGAASV EIIRV                                                  135
```